United States Patent
Freeman et al.

(10) Patent No.: US 7,060,665 B2
(45) Date of Patent: Jun. 13, 2006

(54) WHIPPED CLEANSER AND METHOD OF DISPENSING THE SAME

(75) Inventors: Faith Freeman, Huntington Beach, CA (US); Scott H. Freeman, Huntington Beach, CA (US); Frank H. Asbury, Anaheim, CA (US)

(73) Assignee: Primal Elements, Inc., Garden Grove, CA (US)

(*) Notice: Subject to any disclaimer, the term of this patent is extended or adjusted under 35 U.S.C. 154(b) by 330 days.

(21) Appl. No.: 10/694,545

(22) Filed: Oct. 27, 2003

(65) Prior Publication Data

US 2005/0090411 A1    Apr. 28, 2005

(51) Int. Cl.
C11D 17/00    (2006.01)

(52) U.S. Cl. .................. 510/130; 510/137; 510/426; 510/428; 510/505; 424/70.1

(58) Field of Classification Search .................. None
See application file for complete search history.

(56) References Cited

U.S. PATENT DOCUMENTS 6,491,933 B1 * 12/2002 Lorenzi et al. ............. 424/401

OTHER PUBLICATIONS

Website, www.dove.com; Dove Beauty Bars with unique one-fourth moisturizing lotion. (2 pages).
Website, www.suncitysoap.com; "Commercial Soap Manufacturing". (4 pages).
Website, www.cleaning101.com; "Manufacturing" 5 page article about soap manufacturing.

* cited by examiner

Primary Examiner—Necholus Ogden
(74) Attorney, Agent, or Firm—Stetina Brunda Garred & Brucker

(57) ABSTRACT

A cleanser is provided which may be a glycerin based cleanser to simulate the consistency, appearance, color and smell of ice cream, sherbet or the like. The cleanser may further be agitated to aerate the cleanser to resemble whipped cream such that combining the ice cream resembling cleanser topped with the whipped cleanser may simulate a conventional sundae. The whipped cleanser may have granulated sugar mixed therein so as to enable the mixture of whipped cleanser and granulated sugar to be used as a natural exfoliant.

17 Claims, 2 Drawing Sheets

WHIPPED CLEANSER AND METHOD OF DISPENSING THE SAME

CROSS-REFERENCE TO RELATED APPLICATIONS

Not Applicable

STATEMENT RE: FEDERALLY SPONSORED RESEARCH/DEVELOPMENT

Not Applicable

BACKGROUND OF THE INVENTION

The present invention relates generally to a cleanser, and more particularly to a cleanser made to resemble ice cream, sherbet or the like to stimulate the odor, visual aspects, and texture of ice cream and to function as a skin cleanser.

Skin cleansers are routinely utilized to clean portions of a human body such as the hands, feet and face. Cleansers may be modified to make the same easier to use and more attractive compared to the actual cleanser base or raw material. For example, cleansers may include various fragrances or coloring to be more aesthetically pleasing to the user. Cleansers may also be packaged in various configurations to make distribution of the cleanser to retail stores and consumers simpler and more efficient. This may be accomplished by individually packaging the cleansers' as solid bars with a plastic or paper outer covering. In the alternative, cleansers may be formed as a semi-viscous fluids such that the cleansers may be dispensed out of a pump bottle by consumers.

The present invention provides alternative embodiments with respect to cleansers to make the same even more attractive to consumers in relation to their visual appearance such as its color and texture, feel, and aroma. Additionally, the present invention provides alternative embodiments with respect to the method of dispensing such cleansers.

BRIEF SUMMARY OF THE INVENTION

In accordance with the present invention, there is provided a detergent/cleanser preferably comprising a glycerin based cleanser and preferably including a colorant. The cleanser may be formed to simulate the consistency of ice cream, sherbet or the like having similar texture, color and odor. The cleanser preferably comprises a mixture of about 10% to about 25% glycerin, about 10% to about 25% Water, about 10% to about 25% Sodium Cocoyl Isethionate, about 10% to about 25% Sorbitol, about 5% to about 10% Propylene Glycol, about 5% to about 10% Disodium Lauryl Sulfosuccinate, about 1% to about 5% Stearic Acid, about 0.5% to about 1% Sodium Chloride, up to 0.1% Pentasodium Pentate. With respect to the colorant, the same may be selected from the group consisting of Red 3 CI#45430, Blue #1 CI#42090, Yellow 5 CI#11380, Yellow 6 CI#1 11390, Blue #2 CI#73015, Red 40 CI# 16035, and combinations thereof such that the cleanser resembles various flavors of ice cream. The detergent/cleanser may then be disposed in various size containers for shipping and ultimate display and dispensing to retail consumers. Preferably, such containers comprise half gallon, one gallon or five gallon containers which are similar in appearance to conventional ice cream containers used in the ice cream trade. Additionally, it is contemplated that various containers will be utilized, each having a different color and/or flavor cleanser therein to simulate differing ice cream and/or sherbet flavors.

The applicants have additionally discovered that the detergent/cleanser may be mechanically agitated such as in a conventional mixer wherein the same is aerated. The agitation and aeration can be utilized to aerate the cleanser to include approximately 20%–75% air therein. Preferably, the aeration is between 30%–50% air which has been found to cause the aerated cleanser to simulate the consistency and appearance of conventional whipped cream. During such agitation and aeration, suitable fragrances and/or colorants can additionally be added such that the resultant whipped cleanser additionally simulates the smell of conventional whipped cream.

In the preferred embodiment, the present invention contemplates dispensing the cleanser and/or whipped cleanser in a manner to simulate the dispensing of ice cream and whipped cream. In this regard, a hand ice cream scoop may be used to obtain a quantity of the cleanser from its storage container. The same may then be placed in a conventional cup, cone or the like. One or more scoops of cleanser may be disposed within the cup and subsequently the whipped cleanser may be disposed over the top of the cleanser disposed within the cup. By this procedure, the consumer is able to select desired fragrances and colors of the cleanser and, in effect, form a cleanser sundae for later use by the consumer.

The applicants have additionally found that the whipped cleanser can additionally be provided with granulated sugar which is retained within the whipped cleanser to serve as a natural exfoliant during the cleansing process. In the preferred embodiment, approximately 10%–50% by weight granulated sugar is mixed with the whipped cleanser. The whipped cleanser of course can be dispensed separately from the non-whipped cleanser or, alternatively, concurrently therewith.

These as well as other features of the present invention will become more apparent upon reference to the drawings as well as as described in the Detailed Description of the Invention.

BRIEF DESCRIPTION OF THE DRAWINGS

An illustrative and presently preferred embodiment of the invention is shown in the accompanying drawings in which.

DETAILED DESCRIPTION OF THE INVENTION

Figure 1:
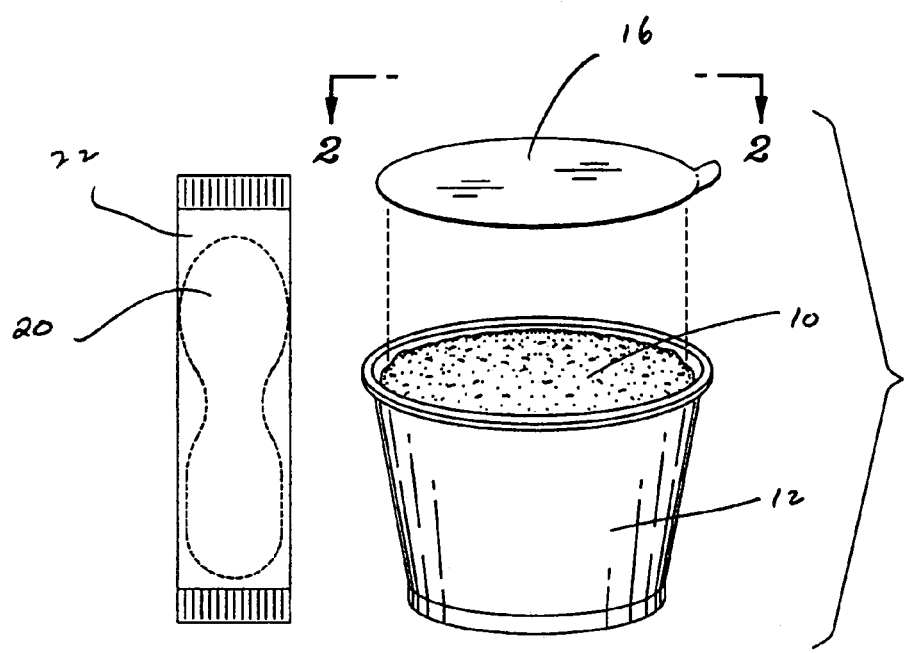
FIG. 1 is a perspective view of the cleanser or the present invention packaged within a personal sized container and lid, and including a dispensing spoon.

FIGS. 1–4 referenced herein are for the purpose of illustrating the preferred embodiments of the present invention and not to limit the same. For example, as shown in FIG. 1, the present invention, which generally relates to a cleanser 10, is dispensed in an twelve ounce container 12. But, the container 12 in which the cleanser 10 may be dispensed or contained may be of other sizes and/or configurations such as a one and/or five gallon container 12, as will be further discussed below.

The cleanser 10 of the present invention may preferably comprise Glycerin, Water, Sodium Cocoyl Isethionate, Sorbitol, Propylene Glycol, Disodium Lauryl Sulfosuccinate, Stearic Acid, Sodium Chloride, Pentasodium Pentate, Tetrasodium Etidronate. This listing of cleanser ingredients is a glycerin based detergent/cleanser, but the cleanser may comprise other ingredients with other base detergents as is used in the trade. These ingredients may be mixed in with each other in the following proportions as follows: Glycerin—about 10% to about 25%; Water—about 10% to about 25%; Sodium Cocoyl Isethionate—about 10% to about 25%; Sorbitol—about 10% to about 25%; Propylene Glycol—about 5% to about 10%; Disodium Lauryl Sulfosuccinate—about 5% to about 10%; Stearic Acid—about 1% to about 5%; Sodium Chloride—about 0.5% to about 1%; Pentasodium Pentate—up to 0.1%, Tetrasodium Etidronate—up to 0.1%. This detergent/cleanser formulation has been found to simulate the texture and consistency of conventional ice cream, sherbet or the like.

Each of the above listed ingredients of the cleanser 10 may be purchased individually and mixed together to have a consistency of ice cream, sherbet or the like with respect to texture. A variety of colorants and fragrances may additionally be mixed into the cleanser 10 such that the cleanser 10 may visually and aromatically resemble various flavors of ice cream.

By way of example and not limitation, the following preferable colorants may be mixed into the cleanser: Red 3 CI#45430, Blue #1 CI#42090, Yellow 5 CI#11380, Yellow 6 CI#11390, Blue #2 CI#73015, Red 40 CI# 16035, or combinations thereof. These as well as other colorants may be mixed into the cleanser 10 to make the cleanser 10 resemble various ice cream flavors such as chocolate, vanilla, chocolate chip, Pralines 'n Cream, or cookies and cream. This list of ice cream and/or sherbet flavors are not the only flavors but are only examples of the numerous possible ice cream flavors that may be visually simulated by the addition of the colorants.

As stated above, the cleanser 10 may have fragrances mixed together with the cleanser 10 such that the cleanser 10 may further resemble ice cream. In particular, by way of example and not limitation, the fragrances may be vanilla, chocolate, grape and other fragrances conventionally used in the trade. This list of fragrances are not the only fragrances that may be added to the cleanser 10 to make the cleanser 10 resemble ice cream and/or sherbet but are merely examples of the numerous possible fragrances that may be mixed into the cleanser 10 to make the cleanser 10 further resemble ice cream.

The detergent/cleanser 10 may be dispensed in various size containers 12 for the purposes of shipping and display to consumers. By way of example and not limitation, the container sizes comprises conventional ice cream containers such as half pint, one pint, eight ounces, twelve ounces, sixteen ounces, half gallon, one gallon, and five gallon containers 12. In this regard, the various sized container 12 may contain or otherwise package the cleanser 10 such that the cleanser 10 may be dispensed for various uses. For example, the smaller sized containers 12 such as the eight ounce container 12 may be utilized by consumers when traveling, and in this regard, the eight ounce container 12 may be regarded as a personal-sized container 12 or a travel-sized container 12. The one and/or five gallon container 12 may be located in stores such that the cleanser 10 may be scooped out into smaller personal-sized containers 12 which further simulate conventional ice cream and are more suitable for consumers.

Figures 2, 3:
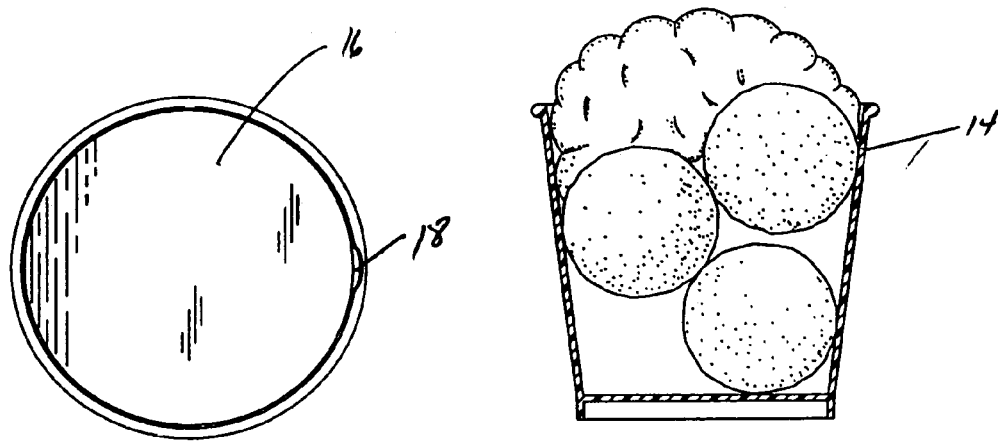
FIG. 2 is a top plan view of the cleanser packaged within the personal sized container.
FIG. 3 is a front cross sectional view of a personal sized container with three scoops of cleanser topped with a whipped cleanser.

More particular, the container 12 may have a similar appearance to ice cream containers 12 used in the trade. These contemporary styled ice cream containers 12 may be used to package the cleanser 10 but alternatively, the containers 12 may be a retro-styled ice cream container 12. For example, the container 12 may be circular with a tapered bottom, as shown in FIG. 1. Ridges may be formed vertically about the circumference of the container 12. The container 12 may have a matching circular lid 16 which may be rigidly secured to the inner circumference at the top of the container 12, as shown in FIG. 2. A tab 18 may be formed at an outer edge of the lid 16 such that it may be pulled to remove the lid 16 from the container 12.

Figure 4:
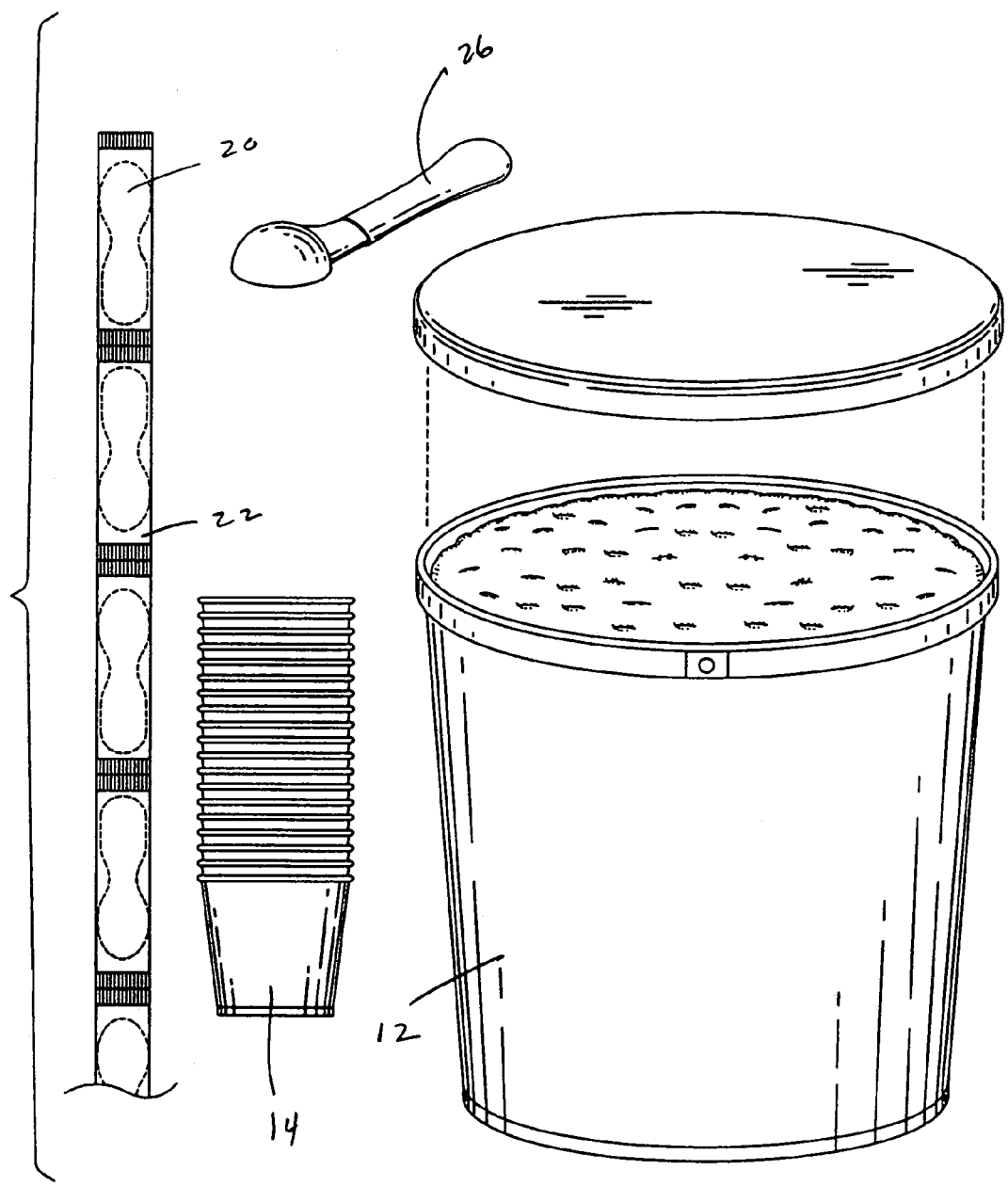
FIG. 4 is a perspective view of a cleanser packaged in a five gallon container with an ice cream scoop, personal sized container and personal sized dispensing spoon attached end to end.

The cleanser 10 is specifically adapted to be sold in retail stores in a manner to simulate the sales of conventional ice cream. In particular, the cleanser 10 may be sold prepackaged in personal-sized containers 12. In this regard, the cleanser 10 may be packaged therein so as to resemble a single, double or triple scoop of ice cream. The triple scoop of cleanser 10 is shown in FIG. 3. A personal sized dispensing spoon 20 (see FIG. 1) may be sold with the personal-sized container 12. The spoon which may be a figure eight wooden spoon 20 may be wrapped in paper or plastic wrapping 22. The wrapping 22 may be connected to each other end-to-end in an accordion style manner, as shown in FIG. 4. The dispensing spoon 20 may be sized and configured to fit within a consumer's hand so that the consumer may spoon out a desired amount of cleanser 10 out of the personal-sized container 12 onto the consumer's hand.

In the alternative, the cleanser 10 may be sold by weight or by volume at the retail stores. For example, the cleanser 10 may be sold to retail stores in industrial sized containers 12 such as five gallon containers. A conventional ice cream scoop 26 may then be utilized to dispense the cleanser from the large container 12 to a smaller, personalized container. For example, a plurality of cleansers 10 simulating different ice cream flavors may be provided in five gallon buckets and placed in carts that resemble conventional refrigerated carts. The consumer may select and purchase desired cleansers 10 and the ice cream scoop 26 may be utilized to scoop out a desired amount of cleanser 10 of each ice cream flavor from the industrial sized container 12 and place the same into the personal-sized container 12 or cup. Additionally, the dispensing spoon 20 may be provided for use with the personal-sized container 12. The dispensing spoon 20 may be attached to each other end-to-end in an accordion style, as shown in FIG. 4, so that the consumer may detach one spoon for later use.

The applicants have discovered that the cleanser 10 may be mechanically agitated to aerate the same. By way of example and not limitation, the cleanser 10 is preferably mechanically agitated with a conventional mixer such as a blender. In this regard, this agitation increases the volume of the cleanser 10 compared to the volume of a cleanser 10 which is not agitated to resemble a foamed food product such as whipped cream-or the like. The cleanser 10 may be agitated until the same includes about 20% to about 75% air. Preferably, the cleanser 10 is agitated until the cleanser is aerated with about 30% to about 50% air which renders the whipped cleanser to have a consistency similar to conventional dairy whipped cream. 100271 The agitated cleanser 10 may further have colorants and fragrances mixed therein to make the agitated cleanser 10 further resemble whipped cream with respect to its visual appearance and odor. These colorants and fragrances may be the same colorants and fragrances added to the cleanser 10 to make the same resemble ice cream, as discussed above. Moreover, the types of colorants and fragrances that may be mixed into the agitated cleanser 10 is not limited by the expressed colorants and fragrances listed above, but other colorants and fragrances may be mixed into the agitated cleanser 10 to resemble other types of whipped products.

The agitated cleanser 10 having a consistency of whipped cream may also have mixed therein a granulated food product. In particular, the agitated cleanser 10 may preferably be mixed with a granulated sugar, and in this regard, this mixture may be used as a natural exfoliant during the cleansing process. The granulated food product such as granulated sugar may preferably be mixed into the agitated cleanser 10 in the amount of about 10% to about 50% of the cleanser or modified cleanser by volume.

As discussed above, the cleanser 10 may be formed to resemble ice cream and various ice cream flavors. Additionally, the cleanser 10 may be formed to resemble whipped cream and other various ice cream toppings. In this regard, ice cream resembling cleanser 10 may be dispensed in conjunction with the whipped cream resembling cleanser 10 such that the combination may resemble a sundae. Further, the whipped cream resembling cleanser 10 may be sold along side the ice cream resembling cleanser 10 at retail stores such that the consumer may select desired flavors and fragrances of whipped cream resembling cleanser 10 to match the selected flavors of ice cream resembling cleansers 10. In particular, the consumer may scoop out or have sales personnel scoop out selected cleansers 10 resembling ice cream of various ice cream flavors and top it with selected cleanser 10 resembling whipped cream so as to form a sundae. In the alternative, the ice cream resembling cleanser 10 may be sold separately from the whipped cream resembling cleanser 10.

This description of the various embodiments of the present invention is presented to illustrate the preferred embodiments of the present invention, and other inventive concepts may be otherwise variously embodied and employed. The appended claims are intended to be construed to include such variations except insofar as limited by the prior art.

What is claimed is:

1. A sundae resembling cleanser comprising
   a. a mixture of about 10% to about 25% glycerin, about 10% to about 25% water, about 10% to 25% sodium cocoyl isethionate, about 10% to 25% sorbitol, about 5% to about 10% propylene glycol, about 5% stearic acid, about 0.5% to about 1% sodium chloride and pentasodium pentate; and
   b. a colorant added to the cleanser and mixed therein to impart on the cleanser a visual appearance of ice cream.

2. The sundae resembling cleanser of claim 1 wherein the colorant may be selected from the group consisting of Red 3 CI#45430, Blue #1 CI#42090, Yellow 5 CI#11380, Yellow 6 CI#11390, Blue #2 CI#73015, Red 40 CI#16035, and combinations thereof such that the cleanser resembles ice cream.

3. The sundae resembling cleanser of claim 1 further comprising a fragrance added to the cleanser and mixed therein to impart on the cleanser an odor of ice cream.

4. The sundae resembling cleanser of claim 3 wherein the fragrance may be vanilla, chocolate or grape.

5. The sundae resembling cleanser of claim 1 wherein the cleanser further comprising an agitated cleanser formed to resemble whipped cream covering the cleanser.

6. The sundae resembling cleanser of claim 5 wherein the agitated cleanser is agitated until the agitated cleanser has about 20% to about 75% air.

7. The sundae resembling cleanser of claim 5 wherein the agitated cleanser is agitated until the agitated cleanser has about 30% to about 50% sir.

8. The sundae resembling cleanser of claim 1 further comprising:
   a. a personal-sized container to package the cleanser and colorant; and
   b. a dispensing spoon adjacent to the personal-sized container.

9. The sundae resembling cleanser of claim 8 wherein the personal sized scooper is attached externally to the personal sized container.

10. The sundae resembling cleanser of claim 8 wherein the personal-sized container has a volumetric size selected from the group consisting of eight ounce, twelve ounce, sixteen ounce, half pint, one pint, half gallon, one gallon, and five gallon.

11. The sundae resembling cleanser of claim 1 further comprising:
    a. an industrial-sized container to package the cleanser and colorant; and
    b. an ice cream scooper adjacent to the industrial-sized container.

12. The sundae resembling cleanser of claim 11 wherein the ice cream scooper is attached externally to the industrial sized container.

13. The sundae resembling cleanser of claim 11 wherein the industrial-sized container has a volumetric, size of five gallons.

14. A method of forming a cleanser to resemble ice cream, the method comprising:
    a. providing a mixture of about 10% to about 25% Glycerin, about 10% to about 25% Water, about 10% to about 25% Sodium Cocoyl Isethionate, about 10% to about 25% Sorbitol about 5% to about 10% Propylene Glycol, about 5% to about 10% Disodium Lauryl Sulfosuccinate, about 1% to about 5% Stearic Acid, about 0.5% to about 1% Sodium Chloride, 0.5 to 1.0 Pentasodium Pentate having a consistency of ice cream; and
    b. agitating the mixture with a conventional mixer.

15. The method of claim 14 wherein the agitating step is maintained until the mixture has about 20% to about 75% air.

16. The method of claim 14 wherein the agitating step is maintained until the mixture has about 35% to about 50% air.

17. The method of claim 14 wherein the agitating step is maintained until the mixture has about 70% to about 75% air.

* * * * *